United States Patent
German et al.

(10) Patent No.: US 10,448,866 B1
(45) Date of Patent: Oct. 22, 2019

(54) ACTIVITY TRACKER

(71) Applicants: Marcelo A German, Carmel, IN (US); Mohammed Nabyl Bennouri, Lake Oswego, OR (US); Jie Lian, Beaverton, OR (US)

(72) Inventors: Marcelo A German, Carmel, IN (US); Mohammed Nabyl Bennouri, Lake Oswego, OR (US); Jie Lian, Beaverton, OR (US)

( * ) Notice: Subject to any disclaimer, the term of this patent is extended or adjusted under 35 U.S.C. 154(b) by 213 days.

(21) Appl. No.: 15/396,774

(22) Filed: Jan. 2, 2017

Related U.S. Application Data

(60) Provisional application No. 62/274,356, filed on Jan. 3, 2016.

(51) Int. Cl.
| | |
|---|---|
| *A61B 5/11* | (2006.01) |
| *A61B 5/0205* | (2006.01) |
| *A61B 5/0488* | (2006.01) |
| *A61B 5/053* | (2006.01) |
| *A61B 5/145* | (2006.01) |
| *A61B 5/1455* | (2006.01) |
| *A61B 5/00* | (2006.01) |
| *G10L 15/22* | (2006.01) |

(52) U.S. Cl.
CPC ......... *A61B 5/1118* (2013.01); *A61B 5/0022* (2013.01); *A61B 5/0205* (2013.01); *A61B 5/0488* (2013.01); *A61B 5/0533* (2013.01); *A61B 5/14532* (2013.01); *A61B 5/14551* (2013.01); *G10L 15/22* (2013.01)

(58) Field of Classification Search
CPC ... A61B 5/1118; A61B 5/0022; A61B 5/0205; A61B 5/488; A61B 5/0533; A61B 5/14532; A61B 5/14551; G10L 15/22
USPC ........................................................ 600/595
See application file for complete search history.

(56) References Cited

U.S. PATENT DOCUMENTS

| | | | | |
|---|---|---|---|---|
| 5,839,901 | A * | 11/1998 | Karkanen ........... | G06F 19/3475 434/127 |
| 2002/0133378 | A1* | 9/2002 | Mault ................. | A61B 5/0002 705/3 |
| 2003/0226695 | A1* | 12/2003 | Mault ................. | A61B 5/0002 177/25.16 |
| 2015/0289798 | A1* | 10/2015 | Pacione ............... | A61B 5/0022 600/301 |
| 2015/0339946 | A1* | 11/2015 | Pacione ................ | A61B 5/411 434/236 |

* cited by examiner

*Primary Examiner* — Daniel L Cerioni

(57) ABSTRACT

An electronic device tracks both calorie loss and intake for a user. The device comprises a plurality of sensors to measure user's physical activities, and provides a user interface to allow user input of activities. The device tracks these activities and estimates the calorie burned based on predefined formulas. Also through the user interface, the device allows user to input information about food or drink consumption, and then estimates the corresponding calorie intake. User input of activities and food/drink consumption can be achieved by means of voice. The electronic device also runs a software app which can provide instructions for the user with regards to activities and/or food/drink consumption. In addition, the app allows user to enter weight, together with the tracked calorie intake and loss history data, to adaptively adjust the calorie calculation formulas and the associated parameters.

20 Claims, 7 Drawing Sheets

ACTIVITY TRACKER

FIELD OF THE INVENTION

The inventive subject matter relates generally to an apparatus and method for measuring and tracking calorie loss and/or intake of a user.

BACKGROUND

Regular exercise and good nutrition are both important for personal health. A healthy lifestyle requires the balance between calorie loss (e.g. through exercise) and calorie intake (e.g. through food or drink). A person who wants to lose weight needs to burn more calories than their intake, whereas a person who wants to gain weight needs to take in more calories than their loss.

An activity tracker is a device or application for monitoring and tracking fitness-related metrics such as distance walked or run, calories burned, and in some cases blood sugar levels, heart-beat and quality of sleep. The term is now primarily used for dedicated electronic monitoring devices that are synchronized, in many cases wirelessly, to a computer or smartphone for long-term data tracking, an example of wearable technology.

An activity tracker typically includes one or more sensors that can measure the movement and/or some physiological parameters (e.g. heart rate, etc.) of the user. Based on the measurement data, calculations can be made to estimate the calories burned by the user. These measurement data and the calculated calories burned can be stored in the device and/or the accompanying computing device (e.g. smartphone), for data logging and trending.

While many activity trackers have proprietary algorithms to estimate the calories burned, most of them do not have a convenient way to monitor user's calorie intake. Typically, to track a user's calorie intake, the user must maintain a diary by manually entering his/her food or drink consumption through a computing device (e.g. smartphone). This user input function is typically implemented through a hand interacting interface of the computing device, e.g. the keyboard, keypad, touch screen, etc. However, this method of manual input is inconvenient for the user, as it distracts the user from other activities by shifting attention to the hand interface of the computing device in order to enter the information. Consequently, many users are reluctant or not consistent to use such features to track their calorie intake and therefore discouraged from using these trackers at all.

Another problem associated with most activity trackers is that the tracker only provides information about the estimated amount of calories burned due to activities, without giving more concrete instructions to the user on what actions the user should take in order to achieve his or her personal goal. For example, the activity tracker may notify the user that 1000 calories were burned for the day, but what the user should do next in order to achieve his or her personal goal with regards to calorie intake or loss is left unknown to the user.

Yet another challenge for all existing activity trackers, is that the formulas for estimation of calorie intake and loss are static. In other words, once the corresponding software application (app) is installed in the computing device, the formulas and the associated parameters for estimating user's calorie intake and/or loss are fixed. However, it is known that different people have different physiological profiles, thus their metabolic rates also differ. Even the same person's metabolic rate can change over time. Therefore, a fixed formula for calorie estimation cannot account for such inter- and intra-subject variabilities. Furthermore, many activities that burn calories cannot be measured by the activity tracker, such as physical activities involving isometric exercise and most types of mental work (e.g. reading, thinking, etc.), thus the associated calories burned cannot be accounted for.

SUMMARY OF THE INVENTION

Therefore, there is a need for an improved activity tracker that can overcome the limitations described above.

One objective of this invention is to provide an improved apparatus and method for a user to enter the calorie intake information into the activity tracker with minimal effort or even without the involvement of user's hand.

Another objective of this invention is to enable an activity tracker to provide more concrete and actionable instructions to a user, for example, suggesting an activity for a certain duration and/or a certain amount of a given food/drink for consumption will be more useful.

Yet a further objective of this invention is to offer a solution for an activity tracker to perform more accurate estimation of calorie intake and loss by means of dynamic adjustment of the calorie calculation formulas and the associated parameters.

These objectives can be achieved by the apparatus and method disclosed in the present invention.

According to some embodiments of the inventive subject matter, an electronic device can be used to track both calorie loss and calorie intake of a user. The device, which can be wearable and in sync with another computing device, can comprise a plurality of sensors to measure user's physical activities, such as walking, running, etc. In addition, the device can provide a user interface to allow user input of other activities that cannot be measured by the device, such as isometric exercises, mental tasks, etc. The device can track all these measured and user input activities, and estimate the corresponding calorie burned based on pre-defined formulas. Also through the user interface, the device can allow user to input information about food or drink consumption, and then estimate the corresponding calorie intake. In certain embodiments, user input of activities and food/drink consumption can be achieved by means of voice. The device can automatically recognize user's voice, interpret user's words, and use the interpreted information for estimation of calories. In addition, information regarding food/drink consumption can also be entered through bar code scanning. For example, user can scan the bar code of a product to get information related to the food/drink being consumed, such as the type, brand, ingredient, and quantity of the food/drink.

In certain embodiments, the electronic device, which can be in sync with the computing device, can run a software app which can provide instructions for the user with regards to activities and/or food/drink consumption. The app can compare the estimated calories burned by the user (e.g. via exercise) with the estimated calories taken by the user (e.g. via food/drink) for the day, and further compare these estimates with the daily goal of calorie loss and/or daily limit of calorie intake, both of which can be defined and edited by the user. Based on these comparisons, the device can search a database which contains information regarding calorie burn rate of a plurality of activities and calorie content of a plurality of food/beverage, and then make specific suggestions to the user with regard to further activities and/or food intake at any time of the day.

In certain embodiments, the app can allow the user to enter weight gain or loss information, and then use such information, together with the stored calorie intake and loss history data, to adaptively adjust the calorie calculation formulas and the associated parameters, so that the calculation of calories burned can better predict the weight change of the user in the future and therefore adjust suggestions.

The unique advantages of the present innovation will be appreciated by people of ordinary skill in the art after referring to the written description of the invention in conjunction with the illustrative drawings.

BRIEF DESCRIPTIONS OF THE DRAWINGS

DETAILED DESCRIPTIONS

General Description of the System Components

Figure 1:
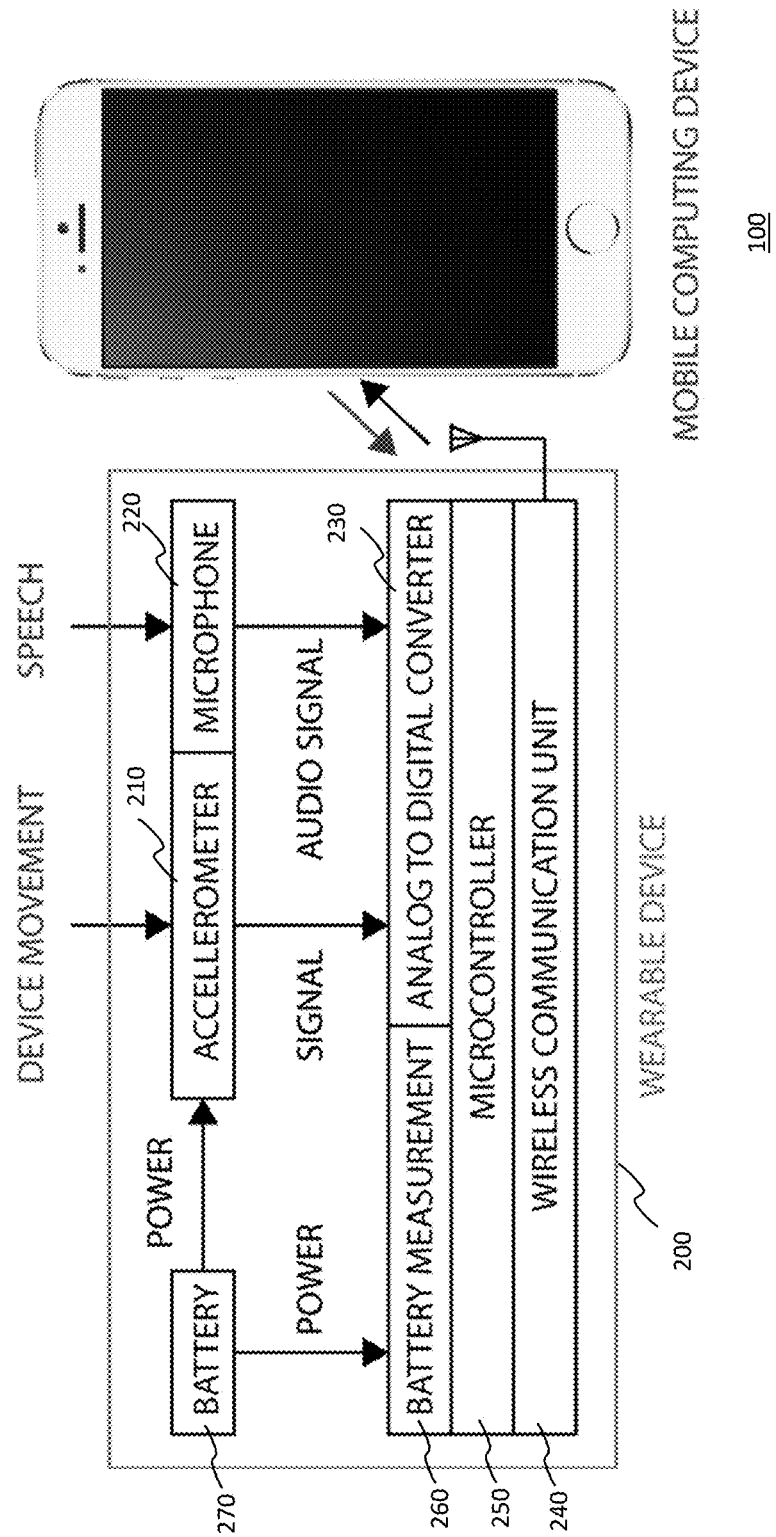
FIG. 1 shows the high-level block diagram of an activity tracker including a wearable unit and a wirelessly connected mobile computing device.

According to a typical embodiment of this inventive subject matter, the improved activity tracker can include a wearable device and a mobile computing device. The wearable device can include a circuitry for measuring the physical activity of the user, for example, by employing one or more motions sensors, such as accelerometers, gyroscopes, magnetometers, inertia sensors, etc. In addition, the wearable device can also include one or more biometric sensors that measure physiological signals of the user, such as the heart rate, respiratory rate, sweating, muscle activity (e.g. via electromyogram), blood sugar and mineral levels, oxygen in blood, etc. As known in the art, data measured by these motion sensors and/or physiological sensors can be correlated to user's activities and used for estimating user's calorie burned.

The wearable device can be capable of wirelessly and bi-directionally communicating with the mobile computing device, such as a smartphone or a tablet computer. As known in the art, the mobile computing device usually has rechargeable battery, a built-in camera, a location/navigation system such as the Global Positioning System (GPS), a user interface for receiving user input (e.g. keypad, microphone, etc.) and generating various types of output, including but not limited to, high resolution display, voice output, user notifications, etc. The mobile computing device can run an operating system (e.g. iOS, Android, etc.) and be capable of wireless connection to a communication network. The mobile computing device can have a software app that can display, store, edit, analyze, and provide summary report of the data collected by the wearable device. Data collected by the wearable device and analyzed by the mobile computing device can include not only user's activities, but also environmental factors such as temperature, humidity, ambient pressure, altitude, etc., which may also affect the metabolic rate thus the calorie burn rate of the user. Based on data measured by the wearable device, the mobile app can calculate the estimated user calories burned, taking into account of personal characteristics, such as age, gender, physical condition, recent history of medication, etc., which may affect individual's metabolic rate. In addition, the mobile computing device can simultaneously track multiple users and/or multiple wearable devices. This may be helpful when one mobile computing device is used to track the calorie balance status of multiple users, each of which is attached with a wearable device, wherein a user may be a person or a pet (e.g. dog, cat, etc.)

Yet according to another embodiment of the inventive subject matter, the activity tracker can be an integrated device that include both the activity tracking unit (including motion and/or physiological sensors) and the mobile computing device. In other words, all the functions of the mobile computing device described above can be physically integrated together with the activity tracking unit, thus eliminating the need of two separate units and the wireless communication between them. For the purposes of illustration, we describe in the following the activity tracker comprising two separate units (i.e. the wearable unit and the mobile computing device) as an example, while it should be understood that the same principle can also be applied to the system with an integrated activity tracking unit and the mobile computing device.

According to one embodiment of the inventive subject matter, the wearable device can be small and lightweight and have an aesthetic design, and can also be waterproof. The wearable device can have a plurality of connecting mechanisms (e.g. clip, button, adhesive surface, etc.) that enable it to be easily adapted to be worn by an individual at various body parts. For example, the wearable unit can be worn as a clothing button, or a necklace, or a headphone/earplug, or wristband, or hat accessory, etc. In another example, the wearable device can be woven into the clothing such as shirts, jackets, scarf, etc., to be part of the so-called smart clothing.

FIG. 1 shows a high-level block diagram of the activity tracker comprising a wearable device 200 and a mobile computing device 100. The user's physical activity can be detected by one or more built-in accelerometers 210, which transform incident device movement information into standard electrical signals (other sensors such as gyroscopes and magnetometers can also be used for movement detection). The signal corresponding to user and/or device movement may be further digitized by an analog-to-digital converter 230. An audio transducer, such as a microphone 220 can be incorporated to transform speech/sound into audio signal. Other sensors such as temperature sensors and optical sensors can also be included into the unit for enhanced system features. All detected sensing signals are processed by a microprocessor 250, and the acquired sensor data can be temporarily stored in a local memory circuit (not shown). The arranged data can then be wirelessly sent to the mobile computing device 100 for post data processing. A wireless communication unit 240 employing a wireless technology standard such as Bluetooth technology can be used to wirelessly transmit and receive data between the wearable unit 200 and the mobile computing device 100. Battery cells 270 such as a battery button cell can be used to power the wearable unit 200. Energy harvesters such as thermal electric generator or solar cell can be used as an alternative source of energy to power the wearable unit 200. The battery measurement block 260 may be included for enhanced features including monitoring the battery usage and determining false operating conditions of the device 200. As described above, the mobile computing device 100 and the wearable device 200 can be integrated into a unitary device to simplify the design and eliminate the need of wireless communication between those separate units.

Voice Input

Many existing activity trackers allow a user to manually enter information regarding food/drink consumption, which is used to estimate the associated calorie intake. User may also enter information regarding physical activities that could not be detected by accelerometers or other sensors. This user input function is typically implemented through a hand interacting interface of a mobile computing device, such as a keyboard, a keypad, a touch screen, etc. Recent advancement includes using sensors to detect hand gestures to capture user's input. However, none of these manual input methods is convenient for the user, as they all distract the user from other activities by shifting attention to the hand interface of the computing device in order to enter the information. Consequently, many users are reluctant or not consistent to use such features to track their calories intake.

Figure 2:
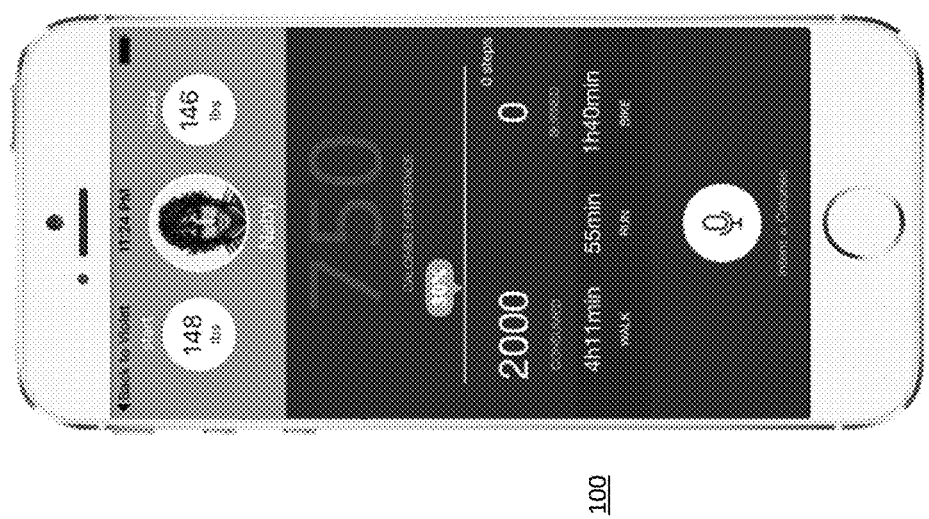
FIG. 2 shows an example of user interface that supports voice input of activities and/or calorie intake information.

According to one embodiment of the inventive subject matter, the activity tracker can provide a voice user interface (VUI) to allow user enter food/drink consumption as well as activities information hand-free. As a non-limiting example, FIG. 2 illustrates one voice user interface displayable on a mobile computing device.

The voice input function can be initially activated by various means. For example, the voice input can be activated by means of a traditional hand input interface, for example, by clicking or tapping on a button. Yet according to certain embodiment of the inventive subject matter, the voice input function can be activated by voice itself. For example, the user can speak a predefined command to a built-in microphone of the activity tracking unit or the mobile computing device. The activity tracking unit or the computing unit can receive the command, interpret through an audio processing algorithm, and then activate the voice input function if the command is verified. An improved voice activation mechanism can also incorporate voice biometric identification, so that only a recognized user's voice command can activate the voice input function. Yet the voice input function can also be activated by combining both hand input and voice input. For example, user may tap the wearable activity tracking unit or the mobile computing device using a pre-specified sequence while giving the voice command simultaneously or following a predefined temporal sequence. The wearable activity tracking unit or the mobile computing device can then analyze the sequence of the hand input and the voice input, and activate the voice input function if the sequence meets the pre-specified criteria.

Figure 3:
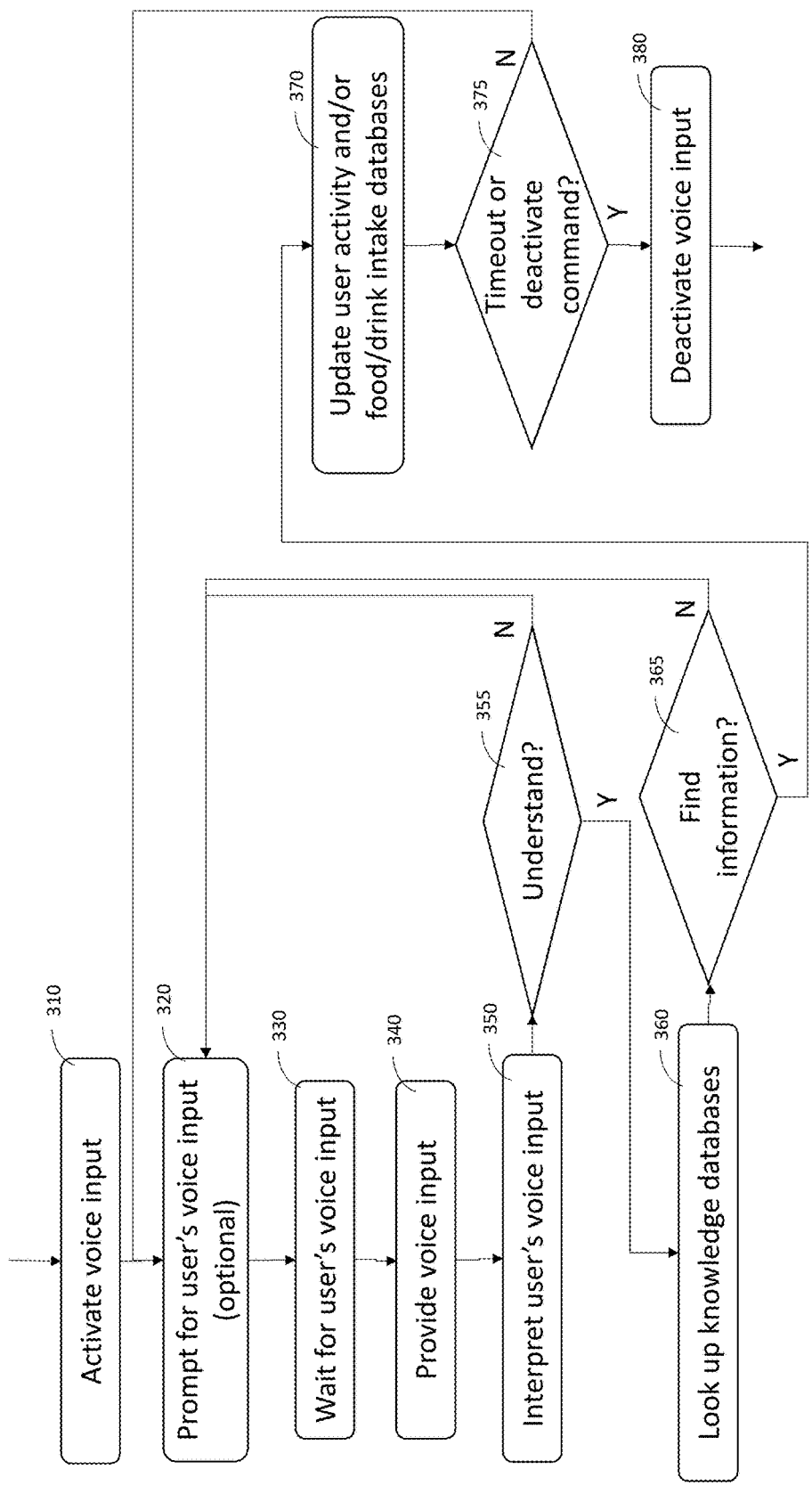
FIG. 3 shows a flow diagram illustrating the process of voice input.

As a non-limiting example, FIG. 3 shows a flow diagram illustrating the general process of voice input. After activation of the voice input function at 310, the activity tracking unit 200 or the mobile computing device 100 can enter a voice input mode, which prepares the user to enter information related to calorie intake and/or loss. Optionally, the activity tracking unit 200 or the mobile computing device 100 can generate voice prompts at 320 that guide user's voice input. For example, the activity tracking unit 200 or the mobile computing device 100 can generate synthesized voice through a built-in speaker to ask the user to enter the type and time spent on an activity, or ask the user to enter the type and amount of food/drink the user took. The activity tracking unit 200 or the mobile computing device 100 then wait for user's voice input at 330. After hearing user's voice at 340 through the built-in microphone, the activity tracking unit 200 or the mobile computing device 100 can attempt to interpret user's spoken words or sentences at 350. A conditional check can be performed at 355. If the user's spoken words or sentences are not understood, then the process can go back to 320 to prompt a new voice input. Otherwise, the activity tracking unit 200 or the mobile computing device 100 can look up knowledge databases at 360 to check if there is relevant information stored therein. If the conditional check at 365 finds no such information is available, then the process can return to 320 to prompt a new voice input. Otherwise, the activity tracking unit 200 or the mobile computing device 100 can update corresponding parameters in a corresponding database at 370 to reflect user's voice input. Thus, to enter information, a user can simply speak to the microphone short sentences or phrases that are within the context of activity/calories tracking. For example, the user can say "I did 30 minutes yoga", or "swimming for one hour". The activity tracking unit 200 or the mobile computing device 100 can receive such voice input, interpret their meanings via a built-in voice recognition software, and then update the database by saving corresponding physical activities (e.g. yoga, swimming) and the associated durations information (e.g. 30 minutes, 1 hour, etc.). By looking up the same or a different knowledge database which stores the estimated calorie burn rate of different types of physical activity, the activity tracking unit 200 or the mobile computing unit 100 can determine the estimated calorie burned by the user through such physical activity. The estimated calorie burned can be further adjusted based on environmental conditions. In one non-limiting example, the originally estimated calorie burned by the user through a physical activity can be adjusted by multiplying a programmable scaling factor based on the measured ambient temperature with respect to a predefined reference temperature. Such an adjustment can more accurately reflect the calorie burn rate that is subject to environmental conditions. For example, the scaling factors can be so programmed that hot ambient temperature can correspond to higher calorie burn rate than cold ambient temperature. In another example, the user can speak "one cup of milk", or "I ate an apple". Similarly, the activity tracking unit 200 or the mobile computing device 100 can recognize the voice input from the user, and update the food/drink intake information (e.g. type and amount) in a corresponding database that stores user's food/drink intake. By looking up the same or a different database which stores the estimated calorie content of a plurality of typical food and drinks, the wearable activity tracking unit 200 or the mobile computing device 100 can determine the estimated amount of calorie intake associated with the food/drink the user consumed. Alternatively, the user can simply say the amount of calories based on a reasonable estimate, e.g. "400 calories", and the wearable activity tracking unit 200 or the mobile computer device 100 can store the amount of calories consumed (e.g. 400 calories) into the database. The activity tracking unit 200 or the mobile computing device 100 can continue to process user's voice input until a predefined timeout period has elapsed without receiving any voice input or after receiving a predefined command (either via voice input or hand input, or their combination) to stop the voice input mode at 375, when the voice input function can be deactivated at 380.

Smart Recommendations

While many existing activity trackers provide information about the estimated amount of calories burned due to activities, none of them gives concrete instructions to the user in a timely manner on what activities the user should engage, or what food/drink the user should take in order to reach calorie balance/goal.

According to certain embodiments of the inventive subject matter, the activity tracker or the mobile computing device can run a software app that can continuously track the user's calorie loss via activities and calorie intake via food and drink, compare these tracked calorie information with a set of parameters that are predefined by the user, search and analyze a database containing estimated calorie burn rate of typical activities and estimated calorie content of typical food/drinks, and then generate a list of recommendations to the user in real time or on demand, so that it can help guide the user to achieve desired status of calorie balance. The following examples, albeit not exclusive, illustrates the operation of smart recommendations feature as described above.

Figure 4:
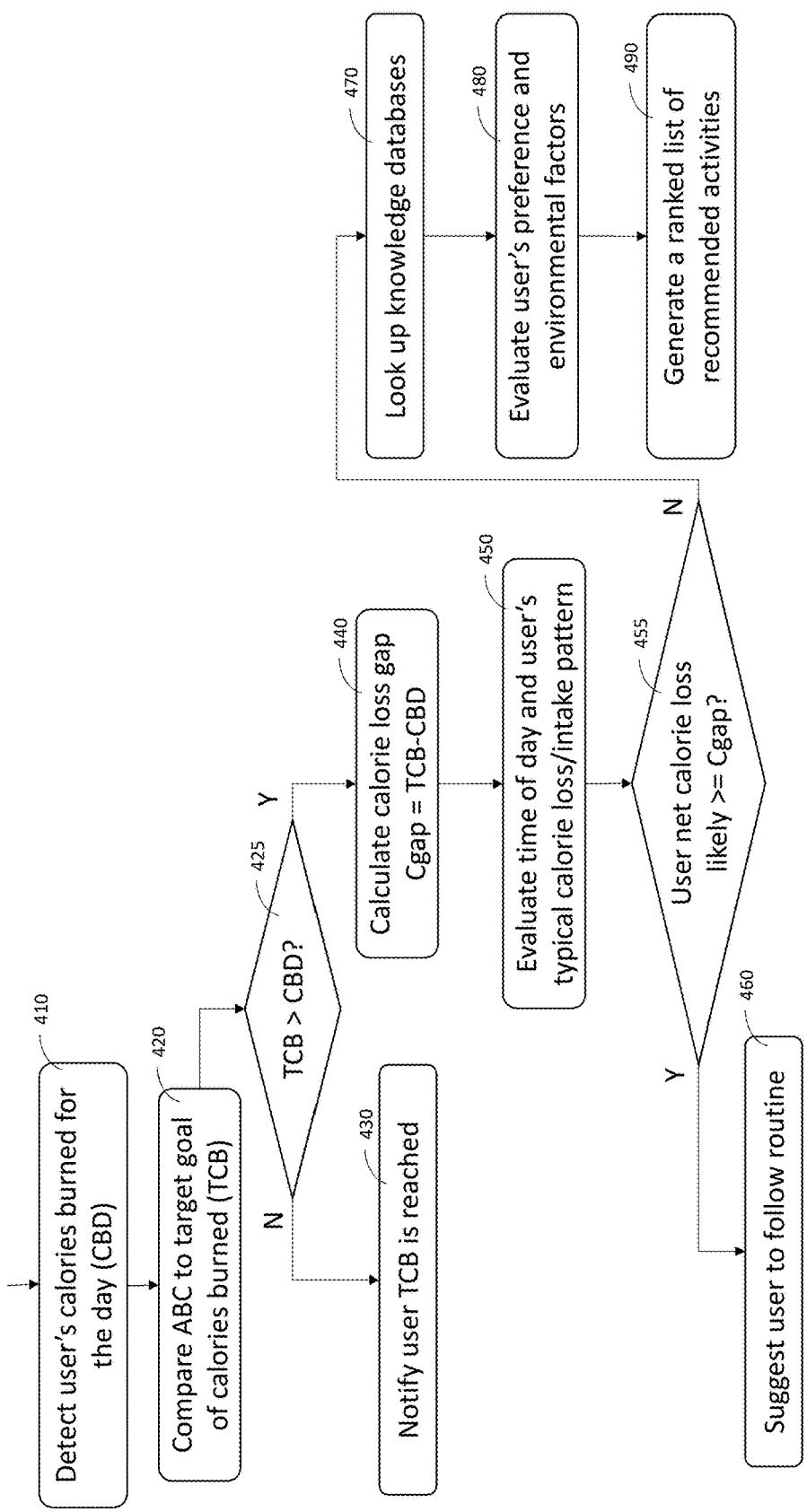
FIG. 4 shows a flow diagram illustrating the process of recommending activities.

In one example as illustrated in FIG. 4, the running app can detect the user's calorie burned for the day (CBD) at 410, and compare it to the target goal of daily calorie burned (TCB) predefined by the user at 420. If the comparison at 425 shows that CBD TCB, then the user can be notified at 430 that the TCB is reached. Otherwise, the app can calculate the calorie loss gap (Cgap), or the difference between TCB and CBD (i.e., Cgap=TCB-CBD) at 440. The app can then evaluate several factors, such as time of the day and user's typical pattern of calorie burned and/or intake for the remaining period of the day (based on the log history data of user's calorie burned and/or intake) at 450, to determine if any specific activities should be suggested to the user. Based on the conditional check at 455, if the user's past behavior indicates that there is a high probability (e.g., based on a predefined probability threshold parameter) that his/her net calorie loss (i.e., calorie burned minus calorie intake) for the remaining period of the day is equal to or greater than Cgap, then a recommendation can be made at 460, suggesting the user to follow his/her routine. On the other hand, if the user's past history indicates his/her net calorie loss for the remaining period of the day is likely less than Cgap, then the app can provide specific suggestions to the user for participating in certain activities. To generate the suggestions, the app can look up a database containing estimated calorie burn rate of typical activities at 470, further taking into account the user's preferred activities which can be pre-selected by the user as well as environmental factors (at 480), and then generate a ranked list of recommended activities for the user at 490. Each entry of suggested activities can show the activity type and the suggested duration, which can be estimated by the ratio between Cgap and the calorie burn rate associated with the selected activity. The rank of the list can be sorted by user's preference (e.g. walking may be more preferable than yoga, etc.) or by suggested duration of the activities (e.g. shorter duration can be ranked higher on the list, etc.) or by other means. Other factors that can be evaluated by the app can include but are not limited to environmental factors such as temperature, ambient pressure, humidity, UV index, etc. The app can determine if certain types of activities should be considered or not considered based on these environmental factors. For example, biking may not be recommended if the weather condition is not suitable for outdoor activities. Alternatively, the app can recommend the combination of multiple activities, so that the estimated total calorie burned from these combined activities is about the same as Cgap.

Figure 5:
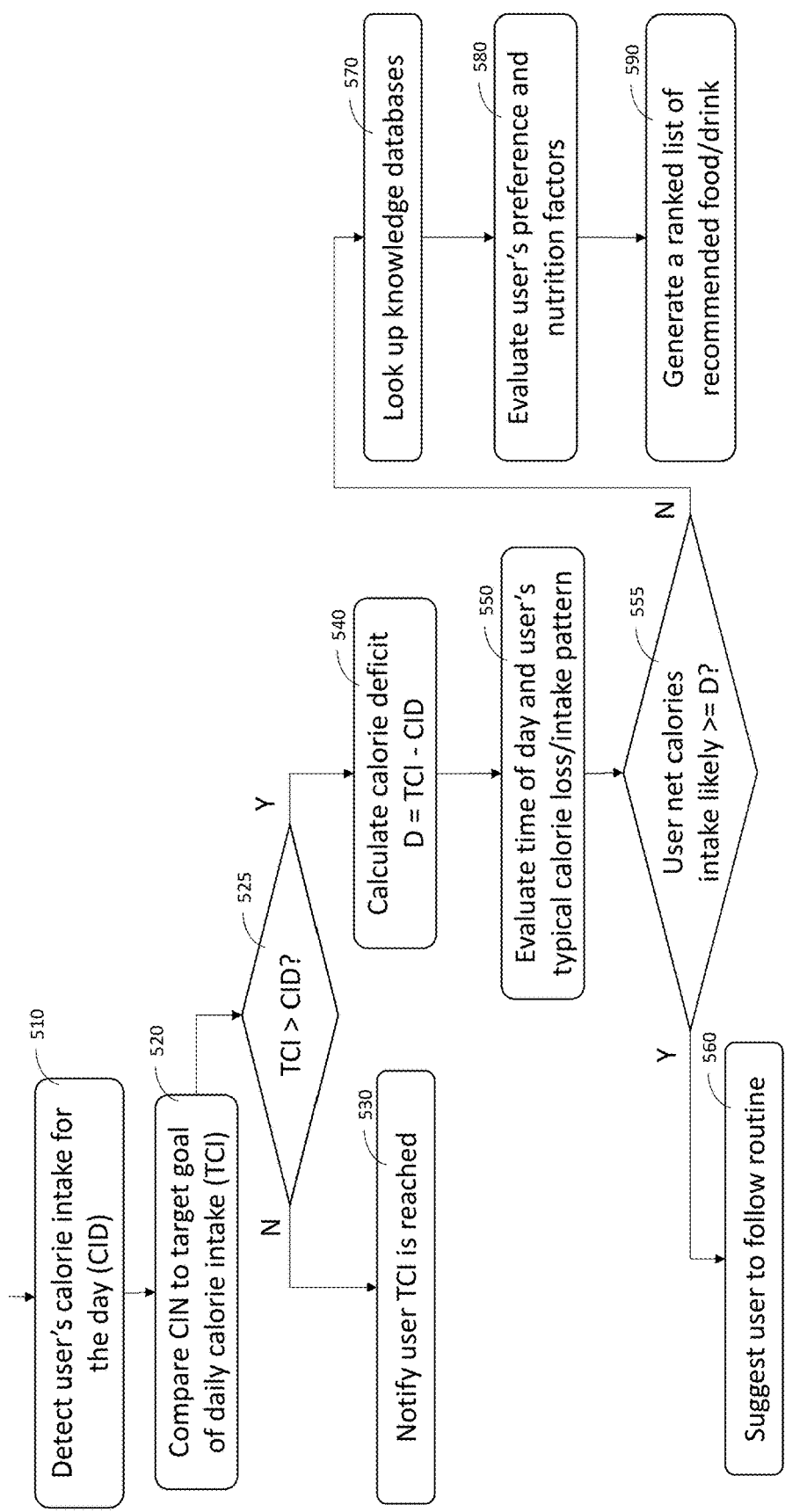
FIG. 5 shows a flow diagram illustrating the process of recommending calorie intake.

In another example as illustrated in FIG. 5, the running app can detect the user's calorie intake for the day (CID) at 510, and compare it to the target goal of daily calorie intake (TCI) at 520. If the comparison at 425 shows that TCI CID, then the user can be notified at 530 that the TCI is reached. Otherwise, the app can calculate at 540 the calorie deficit (D) which is the difference between TCI and CID (i.e., D=TCI-CID). The app can then evaluate several factors, such as time of the day and user's typical pattern of calorie burned and/or intake for the remaining period of the day (based on the log history data of user's calorie burned and/or intake) at 550, to determine if any specific food/drink should be suggested to the user. Based on the conditional check at 555, if the user's past behavior indicates that there is a high probability (e.g., based on a predefined probability threshold parameter) that his/her net calorie intake (i.e., calorie intake minus calorie burned) for the remaining period of the day is equal to or greater than D, then a recommendation can be made at 560, suggesting the user to follow his/her routine. On the other hand, if the user's past history indicates that his/her net calorie intake for the remaining period of the day is less than D, then the app can provide specific suggestions for the user to take certain food and/or drink. To generate the suggestions, the app can look up a knowledge database containing estimated calorie content of typical food/drink at 570, further taking into account the user's preferred food/drink which can be preselected by the user as well as nutrition factors (at 580), and then generate a ranked list of recommended food/drink for the user at 590. Each entry of suggested food/drink can show the type and amount of food/drink the user could take to make up for the calorie deficit. The rank of the list can be sorted by user's preference (e.g. fruit is more preferable than cookie, etc.) or by suggested amount of the food/drink (e.g. smaller serving can be ranked higher on the list, etc.) or by other means. Other factors that can be evaluated by the app include but are not limited to nutrition value of the food/drink, source of the food/drink, etc. The app can determine if certain types of activities should be considered or not considered based on these factors. For example, user may choose to exclude food products with gluten or nut ingredients. Alternatively, the app can recommend the combination of multiple choices of food/drink, so that the estimated total calorie intake from those combined food/drink is about the same as D.

Adaptive Update of Parameters

The metabolic rate varies from person to person. Even for individual subject, his or her metabolic rate also vary from time to time, and may change due to improvement or deterioration of health conditions. Other factors, such as temperature variation, lifestyle change, etc. can also affect a person's metabolic rate. Therefore, adaptive update of formulas and associated parameters for calorie estimation can be advantageous so that the activity tracker can better estimate the calorie intake and/or loss.

It is known that calorie balance means a person consumes the same amount of calories as the calories burned. A person can maintain body weight if calorie remains in balance. One may gain weight if the person consumes more calories than its loss (calorie surplus). On the other hand, one may lose weight if the person burns more calories than its consumption (calorie deficit). Therefore, weight change can be a good indicator of the status of calorie balance. For a typical person, a calorie deficit of approximately 3,500 calories may be needed to lose one pound of body fat.

Energy is expended regardless of the activity, yet the level at which it is done can differ markedly. The number of calories consumed by the body when at rest is referred to as Basal Metabolic Rate (BMR). Calculating the BMR can enable a person to figure out an approximation of the number of calories used to maintain basic body functions. As the BMR may differ from one person to another, according to their age, height, sex, weight and activity level, knowing individual BMR can be critical for maintaining or losing weight. BMR slows down with age as the calorie burning rate. In addition, skipping meals can also decrease the BMR. On the other hand, exercise and regular physical activity can help increase BMR. The individual BMR can be estimated by using the well-known Harris-Benedict equation:

BMR (for men)=66.5+(13.75×weight in kg)+(5.003× height in cm)−(6.755×age in years)

BMR (for women)=655.1+(9.563×weight in kg)+ (1.850×height in cm)−(4.676×age in years)

Alternatively, the BMR can be estimated by using the Harris-Benedict equations revised by Roza and Shizgal:

BMR (for men)=88.362+(13.397×weight in kg)+ (4.799×height in cm)−(5.677×age in years)

BMR (for women)=447.593+(9.247×weight in kg)+ (3.098×height in cm)−(4.330×age in years)

One commonly used method to estimate the total number of calories required for the day to maintain calorie balance is to use the Harris Benedict Formula, which simply multiplies the BMR with the activity factor. There are five variations to the activity factor. The activity ranges from sedentary, light activity, moderate to active to extremely active, with the corresponding activity factor ranges from 1.2 to 1.9. However, this method is not sufficiently accurate since the five levels of activity cannot account for the continuously varying levels of activity.

Figure 6:
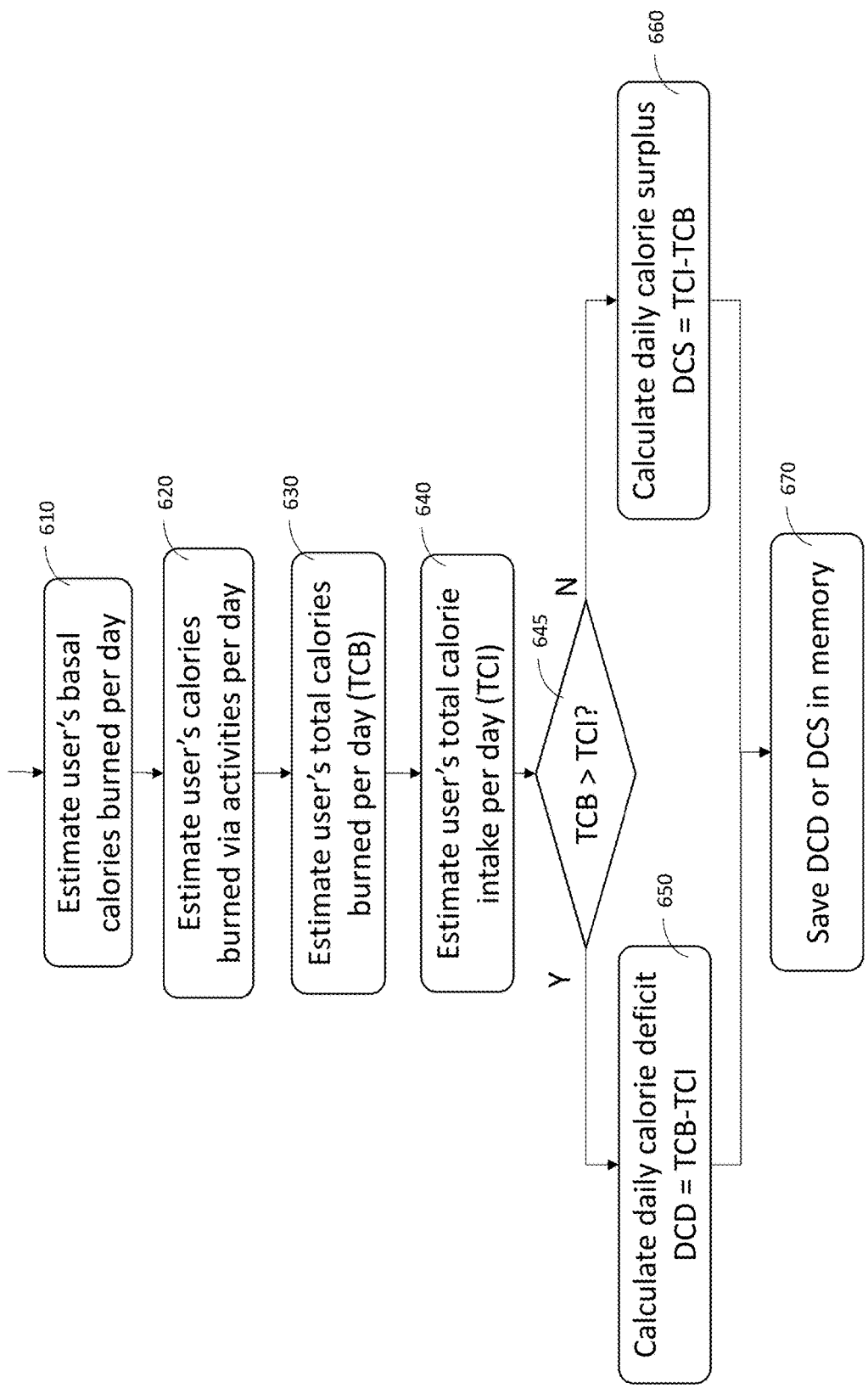
FIG. 6 shows a flow diagram illustrating the process of assessing daily calorie balance.

FIG. 6 shows a flow diagram illustrating the process of assessing daily calorie balance. In one embodiment, the running app can estimate the basal calorie burned per day (BCAL) at 610 by:

BCAL=BMR/(24×60)×TB where TB is the total duration (unit: minutes) per day the user spends in resting condition (including sleep). Thus, BCAL can be an estimate of the total number of calories burned by the user during rest for the day.

At 620, the running app can track all types of activities performed by the user in the day, and estimates the burned calories for each type of activities. The activities tracked by the running app can include physical activities (e.g. running, yoga, etc.) and mental exertions (e.g. reading, typing, etc.). These activities can be tracked by the activity tracker by the built-in sensors or by user input as described above. The running app can then estimate the burned calories corresponding to each type of activities, taking into account both the activity type and the duration of the activity.

At 630, the running app can then estimate the total calories burned per day (TCB) by the user by summing up the contribution of all activities:

TCB=BCAL×KB+sum[ACT(i)×K(i)](i=1 . . . n)

where ACT(i) is the estimated calorie burned by the i-th type activity, K(i) is the predefined scaling factor corresponding to the i-th type activity, n is the total number of types of tracked activities, and KB is a predefined scaling factor corresponding to the resting condition.

At 640, the running app can also calculate the total calories intake per day (TCI) by the user by summing up the contribution of all food/drink consumed by the user:

TCI=sum[c(i)]×KC (i=1 . . . n)

where c(i) is the number of calories contained in the i-th type of food/drink consumed by the user, and KC is a predefined scaling factor. By default, all scaling factors including KC, KB and K(i) can be initially set to 1. But all of these scaling factors can be programmable parameters that can be edited by the user or adjusted by the running app, with a representative but non-limiting range from 0.8 to 1.2.

For each day, a conditional check between total calories burned per day (TCB) and total calories intake per day (TCI) can be performed at 645. Based on the comparison, the running app can calculate the daily calorie deficit (DCD) as DCD=TCB-TCI (if TCB>TCI) at 650, or the daily calorie surplus (DCS) as DCS=TCI-TCB (if TCI>TCB) at 660. The calculated DCD or DCS can then be saved in the memory of the activity tracker at 670, so that they could be displayed or reported to the user, and/or used for adaptive adjustment of parameters for calorie calculation as described more fully below.

According to some embodiments of the inventive subject matter, the running app allows user to enter weight gain or loss information, and then uses such information, together with the stored calorie intake and loss history data, to adaptively adjust the calorie calculation formulas and the associated parameters, so that the calculation of calories loss can better predict the weight change of the user.

Figure 7:
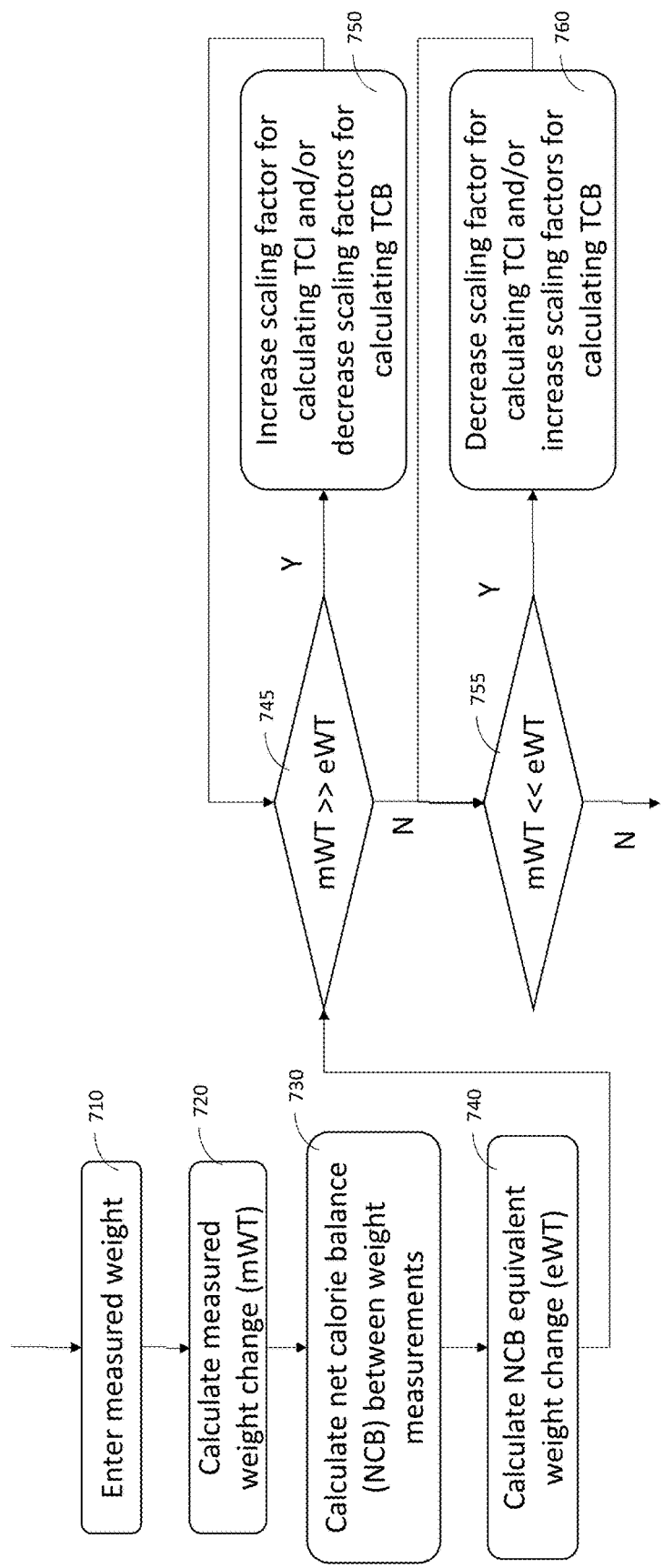
FIG. 7 shows a flow diagram illustrating the process of adjusting parameters for calorie calculation.

For example, FIG. 7 shows a flow diagram illustrating the process of adjusting parameters for calorie calculation. At 710, the user can enter the measured body weight information into the running app. At 720, the running app can calculate the measured weight change (mWT) by comparing the newly entered weight to the previously measured weight. At 730, the running app can calculate the net calorie balance (NCB) between those two weight measurements. The NCB is the algebraic sum of previously saved daily calorie deficit (DCD) and/or daily calorie surplus (DCS) data for each day between the current weight measurement and the immediately preceding weight measurement. At 740, the NCB equivalent weight change (eWT) can be calculated based on the approximation that about 3500 calories correspond to 1 pound of weight. If the conditional check at 745 finds that the measured weight change (mWT) is significantly greater than the equivalent weight change (eWT) (e.g., mWT is greater than eWT by a predefined threshold), then the scaling factor for calculating TCI can be increased, and/or the scaling factors for calculating TCB can be decreased at 750. On the other hand, if the conditional check at 755 finds that the equivalent weight change (eWT) is significantly greater than the measured weight change (mWT) (e.g., eWT is greater than mWT by the predefined threshold), then the scaling factor for calculating TCI can be decreased, and/or the scaling factors for calculating TCB can be increased at 760. Otherwise (i.e., the difference between eWT and mWT is within the predefined threshold), the scaling factors for calculating TCI and TCB can remain unchanged. Each time after adjustment of the TCI and/or TCB scaling factors, the running app can recalculate the NCB and the corresponding eWT using the updated TCI and/or TCB scaling factors. The process can repeat until the difference between eWT and mWT is within the predefined threshold.

For example, if the measured body weight shows that the user has gained certain weight in the past week, the running app can estimate how much total calories surplus is needed to gain such extra weight (e.g. about 3500 extra calories for 1 pound of weight gain, assuming the gained weight is mainly by fat). The running app can then check the stored history information and obtain the net calorie surplus or deficit for the past week by calculating the algebraic sum of DCS or DCD for each day of the past week. If the calculation shows that the net calorie surplus is smaller than the total calorie surplus needed to gain the extra weight, or even the calculation shows the user has a net calorie deficit for the past week, then it suggests the burned calories may be over-estimated, or the user consumed calories may be under-estimated. Accordingly, the formula for estimation of calories can be adjusted. This adjustment could be done manually or automatically by the running app, for example, by reducing one or more parameters of the scaling factors KB and KO to correct overestimation of burned calories, and/or by increasing KC to correct underestimation of consumed calories. After each adjustment of one or more of these scaling factors, the running app can recalculate the net calorie surplus or deficit for the past week using the updated parameters. This adjustment can be repeated until the calculated net calorie surplus for the past week matches the total calorie surplus needed to gain the extra weight.

In another example, based on the user entered information, the running app can detect the user has lost certain weight in the past week. The running app can then estimate how much total calories deficit is needed for the weight loss (e.g. about 3500 calories deficit for 1 pound of weight loss, assuming the weight loss is mainly by fat). The running app can then check the stored history information and obtain the net calorie surplus or deficit for the past week by calculating the algebraic sum of DCS or DCD for each day of the past week. If the calculation shows that the net calorie deficit is smaller than the total calorie deficit needed for the weight loss, or even the calculation shows the user has a net calorie surplus for the past week, then it suggests the burned calories may be under-estimated, or the user consumed calories may be over-estimated. Accordingly, the formula for estimation of calories can be adjusted. This adjustment could be done manually or automatically by the running app, for example, by increasing one or more parameters of the scaling factors KB and KO to correct underestimation of burned calories, and/or by decreasing KC to correct overestimation of consumed calories. After each adjustment of one or more of these scaling factors, the running app can recalculate the net calorie surplus or deficit for the past week using the updated parameters. This adjustment can be repeated until the calculated net calorie deficit for the past week matches the total calorie deficit needed for the weight loss.

The subject matter described herein for providing voice input, providing smart recommendations, and adaptively updating parameters for calorie calculation, etc., may be implemented in hardware, software, firmware, or any combination thereof. As such, the terms "units" or "module" as used herein refer to hardware, software, and/or firmware for implementing the feature being described. In addition, the software "app" may also be implemented in hardware and/or firmware platform.

Persons skilled in the art will recognize that many modifications and variations are possible in the details, materials, and arrangements of the parts and actions which have been described and illustrated in order to explain the nature of the inventive subject matter, and that such modifications and variations do not depart from the spirit and scope of the teachings and claims contained therein.

The principles described above in connection with any particular example can be combined with the principles described in connection with any one or more of the other examples. Accordingly, this detailed description shall not be construed in a limiting sense, and following a review of this disclosure, those of ordinary skill in the art will appreciate the wide variety of systems that can be devised using the various concepts described herein. Moreover, those of ordinary skill in the art will appreciate that the exemplary embodiments disclosed herein can be adapted to various configurations without departing from the disclosed principles.

The previous description of the disclosed embodiments is provided to enable any person skilled in the art to make or use the disclosed innovations. Various modifications to those embodiments will be readily apparent to those skilled in the art, and the generic principles defined herein may be applied to other embodiments without departing from the spirit or scope of this disclosure. Thus, the claimed inventions are not intended to be limited to the embodiments shown herein, but are to be accorded the full scope consistent with the language of the claims, wherein reference to an element in the singular, such as by use of the article "a" or "an" is not intended to mean "one and only one" unless specifically so stated, but rather "one or more". Also, as used herein, "and/or" means "and" or "or", as well as "and" and "or."

All structural and functional equivalents to the elements of the various embodiments described throughout the disclosure that are known or later come to be known to those of ordinary skill in the art are intended to be encompassed by the features described and claimed herein. Moreover, nothing disclosed herein is intended to be dedicated to the public regardless of whether such disclosure is explicitly recited in the claims. No claim element is to be construed as "a means plus function" claim under US patent law, unless the element is expressly recited using the phrase "means for" or "step for".

The inventors reserve all rights to the subject matter disclosed herein, including the right to claim all that comes within the scope and spirit of the following claims:

While the inventor(s) understands that claims are not a necessary component of a provisional patent application, and therefore has not included detailed claims, the inventor(s) reserves the right to claim, without limitation, at least the following subject matter.

We claim:

1. An activity tracker for a user comprising:
   one or more sensors;
   a voice user interface; and
   a processing unit adapted to:
   calculate total calories burned per day (TCB) and total calories intake per day (TCI) of the user;
   calculate a daily calorie deficit (DCD) if TCB is greater than TCI or a daily calorie surplus (DCS) if TCI is greater than TCB, wherein DCD or DCS is a difference between TCB and TCI;
   receive two weight measurements from the user;
   calculate a measured weight change (mWT) between the two weight measurements;
   calculate an equivalent weight change (eWT) based on an algebraic sum of the DCD and DCS for each day between the two weight measurements; and
   automatically adjust a set of TCB scaling factors or a TCI scaling factor based on a comparison between the mWT and eWT;
   wherein TCB is a weighted sum of basal calories burned during a day and calories burned corresponding to a plurality of physical activities of the user during the day, wherein weights of the weighted sum comprise the set of TCB scaling factors, and TCI is a sum of calories intake during the day multiplied by the TCI scaling factor;
   wherein the calories burned corresponding to the plurality of physical activities are derived from measurement by the one or more sensors or a voice input to the voice user interface, and wherein the calories intake is derived from the voice input to the voice user interface.

2. The activity tracker of claim 1, wherein the TCB scaling factors are decreased and/or TCI scaling factor is increased if mWT is greater than eWT by a predefined threshold, and the TCB scaling factors are increased and/or the TCI scaling factor is decreased if mWT is less than eWT by the predefined threshold.

3. The activity tracker of claim 2, wherein the processing unit is adapted to recalculate the eWT after decreasing or increasing of the TCB or TCI scaling factors, and decreasing or increasing of the TCB or TCI scaling factors are repeated until a difference between the eWT and mWT is less than the predefined threshold.

4. The activity tracker of claim 1, wherein the processing unit is adapted to obtain type and duration information of at least some of the plurality of physical activities of the user from the voice input.

5. The activity tracker of claim 1, wherein the processing unit is adapted to obtain type and amount of food or drink intake from the voice input.

6. The activity tracker of claim 1, wherein the one or more sensors comprise a motion sensor adapted to detect at least some of the plurality of physical activities of the user.

7. The activity tracker of claim 6, wherein the motion sensor comprises an accelerometer.

8. The activity tracker of claim 6, wherein the motion sensor comprises a gyroscope.

9. The activity tracker of claim 1, wherein the one or more sensors comprise a biometric sensor adapted to measure one or more physiological signals of the user.

10. The activity tracker of claim 9, wherein the one or more physiological signals comprises any one of a heart rate, a respiratory rate, sweat, electromyogram, blood sugar, and blood oxygen.

11. The activity tracker of claim 1, further comprises a memory storing one or more databases containing calorie conversion information.

12. The activity tracker of claim 11, wherein the calorie conversion information comprises calorie burn rates corresponding to one or more types of physical activity.

13. The activity tracker of claim 11, wherein the calorie conversion information comprises calorie content of one or more types of food or drink.

14. The activity tracker of claim 1 is adapted to enter a voice input mode by receiving a voice command of the user.

15. The activity tracker of claim 1 is adapted to enter a voice input mode by receiving both a hand input and the voice input, wherein the hand input and the voice input follow a predefined temporal sequence.

16. The activity tracker of claim 1, wherein the voice input to the voice user interface is entered without a voice prompt.

17. The activity tracker of claim 1, wherein the one or more sensors comprise an environmental sensor adapted to measure an environmental condition, and the processing unit is adapted to adjust the calories burned corresponding to the plurality of physical activities based on the environmental condition measured by the environmental sensor.

18. The activity tracker of claim 17, wherein the environmental sensor comprises a temperature sensor adapted to measure an ambient temperature, and the processing unit is adapted to multiply the calories burned corresponding to the plurality of physical activities by a temperature-dependent scaling factor, which increases when the temperature sensor detects an increase in the ambient temperature.

19. The activity tracker of claim 1, wherein the processing unit is adapted to track calories burned for a day (CBD), calculate a calorie loss gap by subtracting the CBD from a predefined target goal of daily calories burned, and recommend a ranked list of physical activities to the user if the calorie loss gap is great than zero.

20. The activity tracker of claim 1, wherein the processing unit is adapted to track calories intake for a day (CID), calculate a calorie deficit by subtracting the CID from a predefined target goal of daily calories intake, and recommend a ranked list of food and/or drink to the user if the calorie deficit is great than zero.

* * * * *